United States Patent
Weyl

[11] Patent Number: 6,153,861
[45] Date of Patent: Nov. 28, 2000

[54] HEATING ELEMENT FOR LAMBDA SENSORS

[75] Inventor: Helmut Weyl, Schwieberdingen, Germany

[73] Assignee: Robert Bosch GmbH, Stuttgart, Germany

[21] Appl. No.: 09/362,934

[22] Filed: Jul. 28, 1999

[30] Foreign Application Priority Data

Jul. 28, 1998 [DE] Germany ............ 198 33 862

[51] Int. Cl.[7] .................................. H05B 1/02
[52] U.S. Cl. .................. 219/505; 219/269; 219/476; 219/477; 338/22 R; 338/7; 338/9; 73/204.25; 73/23.31
[58] Field of Search .................. 338/22 R, 7–9; 219/269, 505, 506, 543, 476, 477; 73/204.25, 204.26, 23.31, 31.01, 31.02, 31.05, 31.06

[56] References Cited

U.S. PATENT DOCUMENTS

| | | | |
|---|---|---|---|
| Re. 31,367 | 8/1983 | D'Entremont | 361/27 |
| 4,505,802 | 3/1985 | Mase et al. | 204/425 |
| 4,505,803 | 3/1985 | Mase et al. | |
| 4,512,871 | 4/1985 | Kato et al. | 204/429 |
| 4,891,500 | 1/1990 | Bloore | 219/505 |
| 5,039,839 | 8/1991 | Masaka et al. | 219/270 |
| 5,132,516 | 7/1992 | Hatanaka et al. | 219/270 |
| 5,172,664 | 12/1992 | Mueller et al. | 123/145 A |
| 5,444,219 | 8/1995 | Kelly | 219/505 |
| 5,521,356 | 5/1996 | Bauer | 219/270 |
| 5,656,190 | 8/1997 | Aoki | 219/505 |
| 5,922,232 | 7/1999 | Merz | 219/505 |
| 5,922,287 | 7/1999 | Kato et al. | 422/95 |
| 5,977,525 | 11/1999 | Sahashi | 219/494 |

FOREIGN PATENT DOCUMENTS

| | | |
|---|---|---|
| 35 38 460 | 4/1986 | Germany . |
| 3727469 | 9/1989 | Germany . |
| 3820918 | 12/1989 | Germany . |
| 4040258 | 7/1992 | Germany . |
| 44 20 944 | 1/1996 | Germany . |
| 07919998 | 4/1995 | Japan . |
| 10241836 | 9/1998 | Japan . |

*Primary Examiner*—Teresa Walberg
*Assistant Examiner*—Jeffrey Pwu
*Attorney, Agent, or Firm*—Kenyon & Kenyon

[57] ABSTRACT

A heating element, preferably for oblong plate-shaped sensors for measuring oxygen concentration in internal combustion engine exhaust gas, has a conductive heating strip at one end of the heating element and electrical conductors which are connected electrically to the conductive heating strip and which supply the heating current and provide connection to the other end of the heating element. The positive temperature coefficient of the resistor material of the conductive heating strip is lower than the positive temperature coefficient of the material of at least one section of the conductors.

7 Claims, 1 Drawing Sheet

HEATING ELEMENT FOR LAMBDA SENSORS

FIELD OF THE INVENTION

The present invention relates to a heating element, preferably for oblong plate-shaped sensors for measuring oxygen concentration in the internal combustion engine exhaust gas, having a conductive heating strip at one end of the heating element and electrical conductors which are connected electrically to the conductive heating strip and which supply the heating current and provide connection to the other end of the heating element, and a closed-loop control arrangement for gradually reducing the heating current that flows through a heating element of this kind as it heats up.

BACKGROUND INFORMATION

A heating element is described in German Patent Application No. 44 20 944. The heating element has a preferably oblong plate-shaped ceramic substrate having at least one resistance-type heating element close to one end of the ceramic substrate and two preferably oblong, strip-shaped electrical conductors connected to the resistance-type heating element that extend from the resistance-type heating element's two contact points to the terminals at the other end of the ceramic substrate. The essence of this heating element is as follows: The resistance-type heating element and the electrical conductors are designed as separate units and are made of different materials such that the conductors have a lower positive temperature coefficient of resistance than the resistance-type heating element.

SUMMARY OF THE INVENTION

The heating element of the present invention has the following advantage: The heating element's heat-up time is shortened, with the aim of rendering the sensor ready for control functions more quickly.

Because the positive temperature coefficient of the conductive heating strip's resistance material is lower than the positive temperature coefficient of the resistance material of at least one section of the conductor(s), the conductive heating strip opposite the sensor electrode heats up considerably more quickly, due to the fact that more current flows through this heating zone near the sensor electrode during initial warming, thus heating this area rapidly. As the rear zone, i.e., the section of the conductor(s) connected to the front conductive heating strip, heats up, the current drops automatically.

To achieve the aim of the present invention (an automatic drop in the heating current), the section(s) of the conductors having resistance material with a relatively higher temperature coefficient may be provided either in both conductors or alternatively in just one of the conductors.

Other design features of layout and materials of the above heating element can be the same as those in the heating element described in German Patent Application No. 44 20 944.

In the closed-loop control arrangement that uses the heating element of the present invention, the heating current flowing through the conductive heating strip is reduced gradually in the following manner. During warming, the resistance of the conductor material having the higher temperature coefficient increases to a greater degree than the resistance of the conductive heating strip's resistance material having the lower temperature coefficient. Thus a high current flows through the circuit initially, and the current then subsequently decreases automatically.

Thus it is evident to a person skilled in the art that the current through the heating element's circuit remains approximately constant at its reduced level once temperature equilibrium is reached in the heating element.

DETAILED DESCRIPTION

Figure 1:
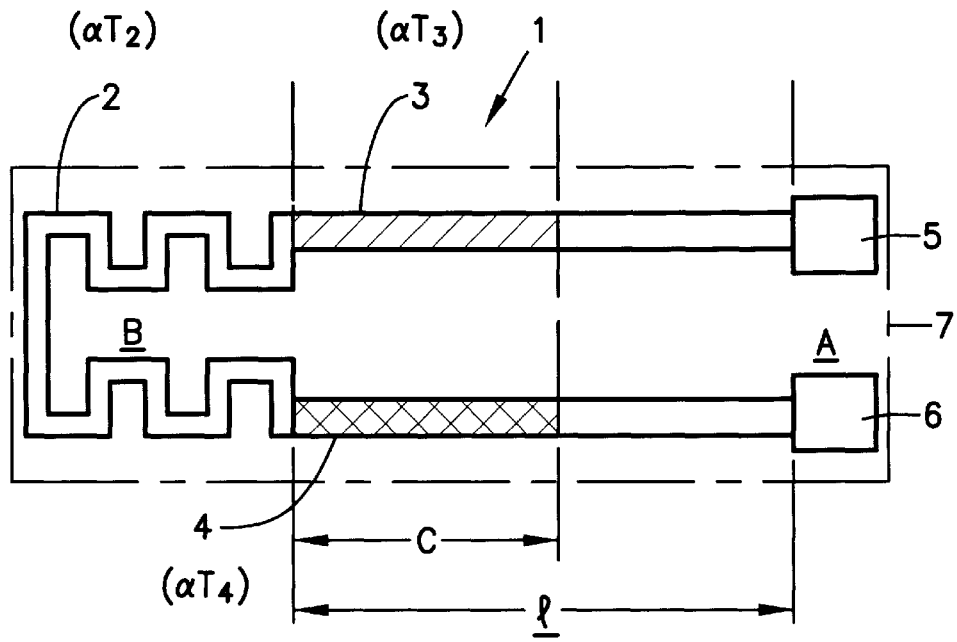
FIG. 1 shows a schematic top view of the layout of an individual heating element of the present invention.

FIG. 1 shows a schematic top-view of an exemplary layout of a heating element shown generally as 1. Heating element 1 is located in or on an oblong plate-shaped ceramic substrate 7 and has, in its front area B, a meandering conductive heating strip 2 made of a resistor material having a relatively lower positive temperature coefficient $\alpha T_2$ and, in the areas connected to the rear end A, a pair of conductors 3, 4 whose resistor material has a temperature coefficient greater than $\alpha T_2$, namely $\alpha T_3$ and $\alpha T_4$, respectively. The conductors 3, 4 end at terminals pads 5, 6 at end A.

It is important to note that, in principle, temperature coefficients $\alpha T_3$ and $\alpha T_4$ may be equal, though this is not absolutely necessary. However, the relationship $\alpha T_3$, $\alpha T_4 > \alpha T_2$ must hold true. In the exemplary embodiment, it is assumed that $\alpha T_3$ and $\alpha T_4$ are equal.

In addition, the resistor material of conductors 3 and 4 having a higher temperature coefficient $\alpha T_3$ and $\alpha T_4$, respectively, does not necessarily have to extend over the entire length l of the conductors. However, it is important that the section of conductors 3 and 4 having the higher temperature coefficient than that of conductive heating strip 2 be connected to the conductive heating strip 2. This is indicated via length C.

However, to simplify the manufacturing process, conductors 3 and 4 are preferably made of the same resistance material having a higher temperature coefficient over their entire length l.

The heating element arrangement shown in FIG. 1 can be manufactured particularly inexpensively by pressing two different resistance layers having the required temperature coefficients onto the surface of ceramic substrate 7 and then fusing them.

Figure 2:
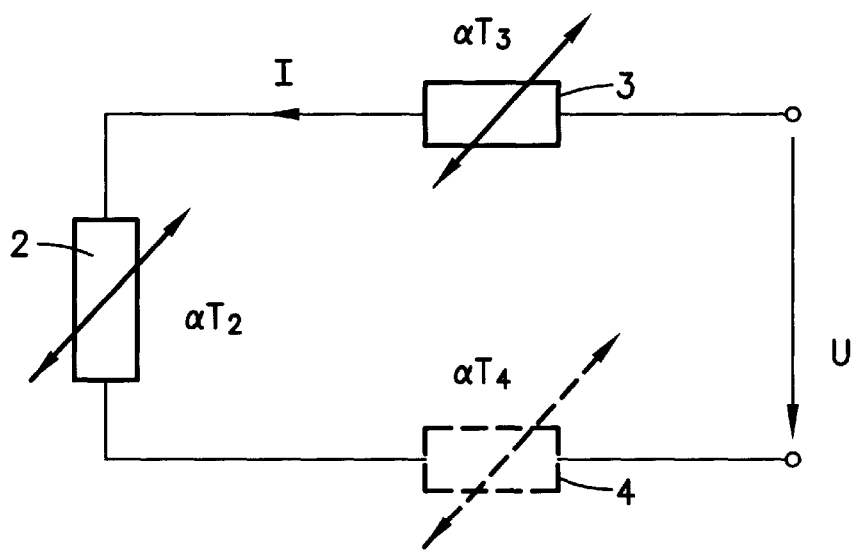
FIG. 2 shows an equivalent circuit diagram of the heating element of the present invention shown in FIG. 1, showing current control characteristics.

In FIG. 2, which shows the equivalent circuit diagram of the heating element shown in FIG. 1, the resistances of the conductive heating strip 2 having the relatively lower temperature coefficient $\alpha T_2$ and of the conductors 3 and 4 having a relatively higher temperature coefficient $\alpha T_3$, $\alpha T_4$, respectively, where $\alpha T_3$ and $\alpha T_4$ can be equal, are shown as concentrated resistances in a circuit.

The temperature changes in resistances 3 and 4 caused by the warming of the resistance in conductive heating strip 2 causes a relatively high current to flow through the heating element during the initial warming phase, thus heating up area B quickly. As resistances 3, 4, i.e., the sections of conductors 3 and 4 having a higher temperature coefficient, heat up, the current decreases automatically, so that no further current control means are required.

It is also important to note that voltage U applied to the circuit in FIG. 2 essentially remains constant. As mentioned above, heating element 1 can be used as a heating element for an oxygen sensor used, for example, to determine the oxygen concentration in the exhaust gas of an internal combustion engine.

What is claimed is:

1. A heating element having a first end and a second end, comprising:
    a conductive heating strip at the first end of the heating element, the heating strip being composed of a resistor material having a first positive temperature coefficient; and
    electrical conductors being electrically connected to the heating strip, supplying a heating current and providing a connection to the second end of the heating element, the conductors including at least one section composed of a material having a second positive temperature coefficient, the first temperature coefficient being lower than the second temperature coefficient.

2. The heating element according to claim 1, wherein the heating element is for an oblong plate-shaped sensor for measuring an oxygen concentration in an exhaust gas of an internal combustion engine.

3. The heating element according to claim 1, wherein the heating strip has a meandering form, and wherein the at least one section of the conductors is directly connected to an area of the heating strip.

4. The heating element according to claim 1, wherein the conductors are composed of a resistor material having a higher temperature coefficient than the resistor material of the heating strip over an entire length of the conductors.

5. The heating element according to claim 1, wherein the electrical conductors include two conductors, only one of the two conductors including the at least one section.

6. A closed-loop control arrangement for gradually reducing a heating current flowing through a heating element during warming, comprising:
    a conductive heating strip forming a first resistor having a first positive temperature coefficient; and
    at least one conductor connected to the heating strip, a second resistor forming at least one section of the at least one conductor, the second resistor being composed of a material having a second positive temperature coefficient, the first temperature coefficient being lower than the second temperature coefficient.

7. The arrangement according to claim 6, wherein the at least one conductor receives a substantially constant voltage during operation.

* * * * *